(12) United States Patent
Soma et al.

(10) Patent No.: US 10,017,817 B2
(45) Date of Patent: Jul. 10, 2018

(54) SKIN ACTIVATION BY ACCELERATION OF PDGF-BB ACTIVITY

(71) Applicant: Shiseido Company, Ltd., Tokyo (JP)

(72) Inventors: Tsutomu Soma, Yokohama (JP); Haruyo Yamanishi, Yokohama (JP); Yumiko Ishimatsu, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 14/857,014

(22) Filed: Sep. 17, 2015

(65) Prior Publication Data

US 2016/0002724 A1 Jan. 7, 2016

Related U.S. Application Data

(62) Division of application No. 13/823,211, filed as application No. PCT/JP2011/071017 on Sep. 14, 2011, now abandoned.

(30) Foreign Application Priority Data

Sep. 17, 2010 (JP) ................. 2010-209705

(51) Int. Cl.
| | |
|---|---|
| C12Q 1/68 | (2018.01) |
| C12Q 1/6876 | (2018.01) |
| G01N 33/50 | (2006.01) |
| A61K 8/67 | (2006.01) |
| A61Q 19/08 | (2006.01) |
| C12Q 1/686 | (2018.01) |

(52) U.S. Cl.
CPC ............ *C12Q 1/6876* (2013.01); *A61K 8/671* (2013.01); *A61Q 19/08* (2013.01); *C12Q 1/686* (2013.01); *G01N 33/5064* (2013.01); *C12Q 2600/148* (2013.01); *C12Q 2600/158* (2013.01)

(58) Field of Classification Search
None
See application file for complete search history.

(56) References Cited

FOREIGN PATENT DOCUMENTS

| CN | 10178582 A | 7/2010 |
|---|---|---|
| JP | 2008-178390 A | 8/2008 |
| KR | 10-2010-0100708 A | 9/2010 |
| WO | WO 98/39035 A | 9/1998 |
| WO | WO 2007/144325 A1 | 12/2007 |
| WO | WO 2008/005533 A2 | 1/2008 |

OTHER PUBLICATIONS

Au, et al. (2009) "Paradoxical Effects of PDGF-BB Overexpression in Endothelial Cells on Engineered Blood Vessels In Vivo", American Journal of Pathology, 175(1): 294-302.*

Lederle, et al. (2006) "Platelet-Derived Growth Factor-BB Controls Epithelial Tumor Phenotype by Differential Growth Factor Regulation in Stromal Cells", The American Journal of Pathology, 169(5): 1767-87.*

Wen, et al. (Jun. 28, 2011) "Morphine Induces Expression of Platelet-Derived Growth Factor in Human Brain Microvascular Endothelial Cells: Implication for Vascular Permeability" PLoS One, 6(6): e21707, 8 pages.*

Fisher et al., "Molecular Mechanisms of Photoaging and its Prevention by Retinoic Acid: Ultraviolet Irradiation Induces MAP Kinase Signal Transduction Cascades that Induce Ap-1-Regulated Matrix Metalloproteinases that Degrade Human Skin In Vivo," J. Invest. Dermatol. Symp. Proc., Aug. 1998, 3(1):61-68.

Guo et al., "Differentiation of adult adipose-derived mesenchymal stem cells into smooth muscle cells induced by PDGF-BB in vitro," Zhongguo Yaowu Linchuang, 2009, 9(4):301-303.

http://www.nlm.nih.gov/medlineplus/druginfo/a682437.html, printed May 15, 2015, last reviews Aug. 1, 2010, Author unknown, published by Medline Plus online, U.S., National Library of Medicine, Bethesda, MD, no journal, no volume, no pages, 4 pages long printed.

Janmaat et al., "Erythopoietin accelerates smooth muscle cell-rich vascular lesion formation in mice through endothelial cell activation involving enhanced PDGF-BB release," 2010 originally online Dec. 14, 2009, Blood, 115(7):1453-1460.

Kim et al., "Antiwrinkle effect of adipose-derived stem cell: Activation of dermal fibroblast by secretory factors," Journal of Dermatological Science, 2009, 53(2):96-102.

Kume et al., "Lysophosphatidylcholine Transcriptionally Induces Growth Factor Gene Expression in Cultured Human Endothelial Cells," J. Clin. Invest, Feb. 1, 1994, 93(2):907-911.

Peled et al., "The Ontogeny of Scarless Healing II: EGF and PDGF-B Gene Expression in Fetal Rat Skin and Fibroblasts as a Function of Gestational Age," Annals of Plastic Surgery, Oct. 1, 2001, 47(4):417-424.

Sasaki et al., "Mesenchymal Stem Cells Are Retruited into Wounded Skin and Contribute to Wound Repair by Transdifferentiation into Multiple Skin Cell Type," Journal of Immunology, 2008, 18:2581-2587.

Schwartz et al., "Topical All-Trans Retinoic Acid Stimulates Collagen Synthesis In Vivo," J. Invest. Dermatol., Jun. 1, 1991, 96(6):975-978.

Soma et al., "Shinpi ni Okeru Kan'yokei Kansaibo no Kyokuzaki to Tokusei ni Kansuru Kaiseki," Regenerative Medicine, Feb. 2010, 9:239, O-37-3.

Tomita et al., "PDGF isoforms induce and maintain anagen phase of murine hair follicles," Journal of Dermatological Science, 2006, 43:105-115.

Wollina, "Topical PDGF-BB results in limited healing in a patient with Werner's syndrome and chronic leg ulcers," Journal of Wound Care, 2004, 13(10):415-416, abstract only.

(Continued)

*Primary Examiner* — Robert M Kelly
(74) *Attorney, Agent, or Firm* — Foley & Lardner LLP

(57) ABSTRACT

This method, which screens drugs that activate the skin, is characterized by causing candidate drugs to act on vascular endothelial cells, and selecting drugs that enhance the expression of PDGF-BB by the cells as a skin activation agent.

2 Claims, 8 Drawing Sheets

(56) References Cited

OTHER PUBLICATIONS

Class-2010 Senior Research Theses, Department of Life Science, Tunghai University, Jul. 2010, pp. 1-20.
Dr. Hsieh Life Log, "Skin Fibroblast," Jun. 18, 2007, 2 pages, with partial English machine translation, 2 pages.

* cited by examiner

SKIN ACTIVATION BY ACCELERATION OF PDGF-BB ACTIVITY

CROSS-REFERENCE TO RELATED APPLICATIONS

This application is a Divisional of U.S. application Ser. No. 13/823,211, now abandoned, which is the U.S. National Stage application of PCT/JP2011/071017, filed Sep. 14, 2011, which claims priority from Japanese application JP 2010-209705, filed Sep. 17, 2010.

The instant application contains a Sequence Listing which has been submitted in ASCII format via EFS-WEB and is hereby incorporated by reference in its entirety. Said ASCII copy, created on Sep. 15, 2015, is named sequence.txt and is 3 KB.

TECHNICAL FIELD

The present invention relates to skin activation by acceleration of platelet-derived growth factor-BB (PDGF-BB) activity.

BACKGROUND ART

Stem cells are cells that have two properties consisting of pluripotency that allows production of cells that differentiate into a plurality of cells, and self-replication that allows production of cells that are identical to those cells. Stem cells derived from embryos, which are the initial development stage of a fertilized egg, are referred to as embryonic stem cells (ES cells). Although human ES cells are expected to be used in regenerative medicine, the production of new human ES cells is not allowed due to ethical considerations involving the use of fertilized eggs.

In recent years, attention has been focused on induced pluripotent stem cells (iPS cells) as cells demonstrating properties similar to those of ES cells. However, the production of iPS cells is associated with numerous problems from the viewpoints of cell malignant transformation, production efficiency and the like. On the other hand, somatic stem cells, which have the ability to differentiate into specific tissue, are not associated with ethical issues in the manner of embryonic stem cells since they are obtained from the patient's own bone marrow or other body tissue.

In the skin, epidermal stem cells (Non-Patent Document 1) are well-known to be present in the epidermal basal layer, and follicular epithelial stem cells (Non-Patent Document 2) and melanocyte stem cells (Non-Patent Document 3) have been reported to be present in regions referred to as bulge regions of hair follicles. On the other hand, although fibroblasts having a long, narrow spindle shape are present in fibrous components of the skin consisting mainly of collagen, it has not yet been determined as to whether stem cells are present in dermal fibroblasts. In addition, although skin-derived precursors (SKP) are known to exist that differentiate into a plurality of cell lines such as those of fat, glia, cartilage or muscle (Non-Patent Document 4), the correlation between dermal fibroblasts and SKP has not been determined.

Since mesenchymal stem cells, which are isolated from bone marrow as fibroblast precursors (Non-Patent Document 5), differentiate into various cells belonging to mesenchymal cell lines (including osteocytes, myocytes, chondrocytes, tendon cells and adipocytes), they are expected to be applied to regenerative medicine such as the reconstruction of bone, blood vessels and muscle. More recently, mesenchymal stem cells have been determined to have the potential of being present in numerous tissues having mesenchymal tissue, and have been isolated from fat, umbilical cord blood and the placenta (Non-Patent Documents 6 to 8). However, the presence of mesenchymal stem cells in the dermis has yet to be determined.

PRIOR ART DOCUMENTS

Non-Patent Documents

Non-Patent Document 1: Watt, F. M., J. Dermatol. Sci., 28: 173-180, 2002
Non-Patent Document 2: Cotsarelis, G., et al., Cell, 57: 201-209, 1989
Non-Patent Document 3: Nishimura, E. K., et al., Nature, 416: 854-860, 2002
Non-Patent Document 4: Wong, C. E., et al., J. Cell Biol., 175: 1005-1015, 2006
Non-Patent Document 5: Pittenger, M. F., et al., Science, 284: 143-147, 1999
Non-Patent Document 6: Park, K. W., et al., Cell Metab., 8: 454-457, 2008
Non-Patent Document 7: Flynn, A., et al., Cytotherapy, 9: 717-726, 2007
Non-Patent Document 8: Igura, K., et al., Cytotherapy, 6: 543-553, 2004
Non-Patent Document 9: Kim, W. S., et al., J. Dermatol. Sci., 53: 96-102, 2009
Non-Patent Document 10: Dalla-Favera, R., et al., Nature, 292: 31-35, 1981

SUMMARY OF THE INVENTION

Mesenchymal stem cells have been determined to also be present in fat in addition to bone marrow, umbilical cord blood and the placenta. Mesenchymal stem cells have also been determined to be present in the dermis in the same manner as subcutaneous fat located below the dermis, and further determined that they locally present at vascular sites. However, the mechanism by which these mesenchymal stem cells of the dermis and fat are locally present at vascular sites, as well as the reason why these stem cells increase or decrease with aging, are unknown. Thus, an object of the present invention is to determine the reason for increases or decreases in mesenchymal stem cells in the dermis and subcutaneous fat caused by aging, and provide a method for improving skin condition by regulating those factors involved in maintaining mesenchymal stem cells at these sites.

Since the number of bone marrow mesenchymal stem cells is extremely low and sources of umbilical cord blood and placentas are limited, there are limitations on the available sources of self-derived mesenchymal stem cells. If mesenchymal stem cells were able to be isolated from the dermis, the skin could serve as a valuable supply source of mesenchymal stem cells used in regenerative medicine and aesthetic medicine. In this connection, we demonstrated that mesenchymal stem cells are also present in the dermis in the same manner as subcutaneous fat, and established a method for isolating these mesenchymal stem cells present in the dermis and subcutaneous fat (Japanese Patent Application No. 2009-213921). Since the mechanism by which these dermal and subcutaneous fat-derived mesenchymal stem cells are locally present at vascular sites, as well as reasons for increases and decreases in these stem cells caused by aging, are unknown, when the inventors of the present invention conducted studies for the purpose of identifying in greater detail those sites where mesenchymal stem cells are present in dermis or subcutaneous fat and determining those factors that cause localization of mesenchymal stem cells, it was determined that PDGF-BB is involved. CD34-positive dermal and subcutaneous fat-derived mesenchymal stem cells decreased with aging, and PDGF-B gene expression also similarly decreased with aging. Ameliorative effects on wrinkles and other forms of skin aging have been reported by injecting fat-derived mesenchymal stem cells into aged skin (Non-Patent Document 9). Also, fat-derived mesenchymal stem cells have been determined to demonstrate an antioxidant function in the skin. On the basis thereof, skin aging can be inhibited by enhancing the expression of endogenous PDGF-BB at vascular sites where dermal and subcutaneous fat-derived mesenchymal stem cells are present locally, and more specifically, in vascular endothelial cells that highly express PDGF-BB, and maintaining a large number of mesenchymal stem cells in the dermis and subcutaneous fat.

Thus, the present application includes the following inventions:

[1] a method for screening drugs that activate skin, comprising allowing a candidate drug to act on vascular endothelial cells, and selecting the drug that accelerates expression of PDGF-BB by the cells for use as a skin activator;

[2] the method of [1], wherein the selection is carried out by measuring mRNA derived from PDGF-B in the cells by real-time polymerase chain reaction;

[3] a method for inhibiting skin aging by activating mesenchymal stem cells, and thereby activating skin, by increasing the activity or level of PDGF-BB at a vascular site of the skin; and,

[4] the method of [3], wherein retinoic acid is applied to skin for which aging is desired to be inhibited;

A novel skin activator can be identified by the present invention.

EMBODIMENTS OF THE INVENTION

Figure 1:
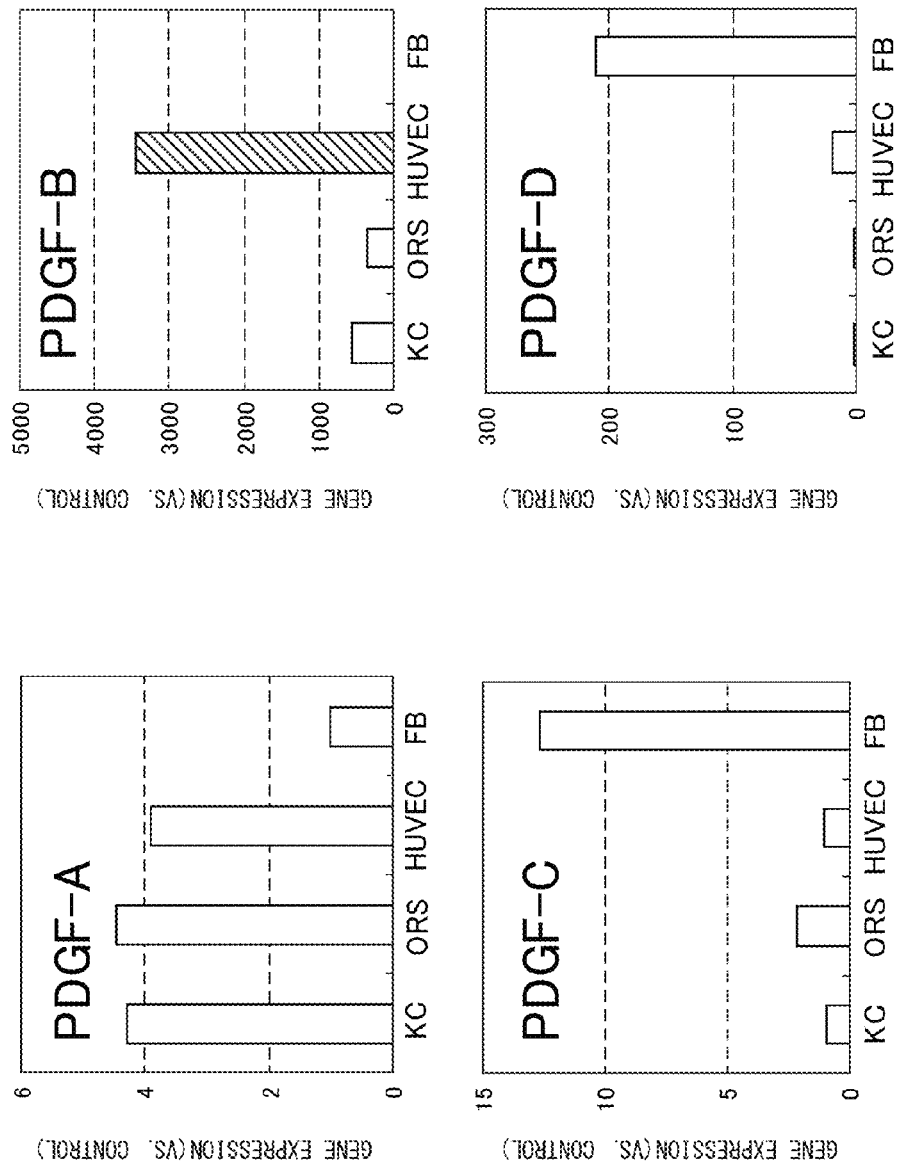
FIG. 1 indicates expression of PDGF gene in vascular endothelial cells.

The present invention relates to a method for screening drugs that activate skin, comprising allowing a candidate drug to act on vascular endothelial cells, and selecting the drug that accelerates expression of PDGF-BB by the cells for use as a skin activator.

Platelet-derived growth factor is a growth factor involved in regulation of migration, proliferation or the like of fibroblast, smooth muscle cells, glial cells and other mesenchymal cells, and is produced by various cells such as epithelial cells or endothelial cells. Although there are at least four types of PDGF, consisting of PDGF-A, PDGF-B, PDGF-C and PDGF-D, there are also three types of isoforms (PDGF-AA, PDGF-AB and PDGF-BB) resulting from the adoption of a homo- or hetero-dimer structure as a result of the A chain and B chain forming disulfide bonds. PDGF is known to express its physiological action through PDGF receptor (PDGFR) which is a tyrosine kinase-associated receptor. PDGF-B gene is known and has been cloned (Non-Patent Document 10).

The mesenchymal stem cells used in the present invention can be derived from the dermis of all species of mammals, including humans, chimpanzees, other primates, domestic animals such as dogs, cats, rabbits, horses, sheep, goats, cows and pigs, as well as laboratory animals such as rats, mice and guinea pigs.

Although there are no particular limitations thereon, activation of skin as referred to in the present invention generally refers to a state in which metabolism of skin tissue becomes active, the turnover period becomes comparatively short, and tissue fatigue, atrophy and the progression of oxidation are reduced. As a result of tissue activation, skin tightness can be maintained and the formation of wrinkles and age spots can be prevented and alleviated.

Expression of PDGF-BB gene in vascular endothelial cells may be determined by, for example, measuring the level of PDGF-BB. Preferably, this measurement can be carried out by a method commonly known in the relevant technical field using an antibody specific to PDGF-BB, examples of which include various methods such as immunostaining using a fluorescent substance, pigment, enzyme or the like, Western blotting or immunoassay such as ELISA or RIA. In addition, this can also be determined by extracting total RNA from vascular endothelial cells, and measuring the amount of mRNA that encodes PDGF-B. Extraction of mRNA and measurement of the amount thereof are commonly known in the relevant technical field, and for example, quantification of RNA is carried out by quantitative polymerase chain reaction (PCR) such as real-time polymerase chain reaction (RT-PCR). Selection of primers suitable for RT-PCR can be carried out by a method commonly known among persons with ordinary skill in the art.

The inventors of the present invention found that retinoic acid accelerates expression of PDGF-BB. Thus, selection of a skin activator can be carried out by investigating by means of statistical techniques and the like whether or not a candidate drug accelerates expression of PDGF-BB by comparing with a positive control, which uses a drug such as retinoic acid having an effect of accelerating expression of PDGF-BB, and a negative control, which uses a drug such as siRNA of PDGF-B gene having an effect of inhibiting expression of PDGF-BB.

Moreover, the present invention also provides a method for evaluating a candidate drug for the ability to accelerate expression of a polynucleotide capable of hybridizing under highly stringent conditions with a polynucleotide that encodes PDGF-B (SEQ ID NO: 1) in vascular endothelial cells, and selecting a candidate drug that has that accelerating ability for use as a skin activator. Hybridization can be carried out in accordance with a commonly known method or method applicable thereto, such as the method described by Sambrook, et al. in Molecular Cloning 2nd Edition, Cold Spring Harbor Lab. Press, 1989, and highly stringent hybridization conditions refer to conditions consisting of, for example, a sodium concentration of about 10 mM to 40 mM and preferably about 20 mM, and a temperature of about 50° C. to 70° C. and preferably about 60° C. to 65° C.

Moreover, the present invention also relates to an aesthetic method for activating skin and thereby inhibiting skin by increasing the activity or level of PDGF-BB at vascular sites of skin to allow PDGF-BB, for which activity has been accelerated or expression level has been increased, to act on mesenchymal stem cells and activate the mesenchymal stem cells as a result thereof. As previously described, the inventors of the present invention found that retinoic acid, and particularly tretinoic acid, accelerates expression of PDGF-BB. Thus, this method is carried out by applying tretinoic acid to, for example, skin for which aging is desired to be inhibited.

In addition, when a gene encoding PDGF-B in a specimen is in an inactive state or dormant state and cells are deficient or lacking in PDGF-B as a result thereof, the activity or level of PDGF-BB can be increased by using a vector incorporating PDGF-BB gene in order to introduce the PDGF-B gene per se into cells. In this vector, a regulatory sequence, such as a promoter or enhancer that accelerates expression of PDGF-B gene is preferably arranged at a location that enables it to act on the PDGF-B gene.

Either a gene insertion method using a viral vector or a non-viral gene insertion method (Nikkei Science, April 1994, pp. 20-45; Experimental Medicine Special Issue, 12(15), 1994; Experimental Medicine Supplement, "Basic Technologies of Gene Therapy", Yodosha Co., Ltd. (1996)) can be applied for introducing the PDGF-B gene into cells. Examples of gene insertion methods using a viral vector include methods consisting of incorporating DNA encoding PDGF-B and inserting into a DNA or an RNA virus such as a retrovirus, adenovirus, adeno-associated virus, herpes virus, vaccinia virus, pox virus, polio virus or sinbis virus. Among these, methods using retrovirus, adenovirus, adeno-associated virus and vaccinia virus are particularly preferable. Examples of non-viral gene insertion methods include a method consisting of intramuscular administration of an expression plasmid (DNA vaccine method), liposome method, lipofectin method, microinjection method, calcium phosphate method and electroporation, and the DNA vaccine method and liposome method are particularly preferable. In addition, in vivo methods, in which DNA is introduced directly into cells, and ex vivo methods, in which a certain type of cells are extracted from a human, DNA is introduced into the cells outside the body, and the cells are then returned to the body (Nikkei Science, April 1994, pp. 20-45;

Japan Medicine Monthly, 36(1), 23-48 (1994), Experimental Medicine Special Issue, 12(15) (1994)), are used in order to allow the aforementioned gene to actually act as a pharmaceutical. In vivo methods are more preferable. In the case of administering by an in vivo method, administration can be made, for example, intravenously, intraarterially, subcutaneously, intracutaneously or intramuscularly. In the case of administering by an in vivo method, administration is typically made in the form of an injection preparation and the like, and a commonly used vehicle may be added as necessary. In addition, in the case of administering in the form of liposomes or fusogenic liposomes (such as Sendai virus-liposome fusion products), administration can be in the form of a liposome preparation such as a suspension, frozen preparation or centrifugally separated frozen concentrate.

Examples

The following provides a more detailed explanation of the present invention through examples thereof. Furthermore, the present invention is not limited thereby.

Experimental Methods

Measurement of PDGF-B Gene Expression Level in Human Skin Constituent Cells

The expression level of PDGF-B gene in constituent cells of human skin was investigated by quantitative PCR. Epidermal keratinocytes KC and follicular epithelial cells in the form of hair follicle outer root sheath cells ORSC were cultured using EpiLife-KG2 medium (Kurabo Industries Ltd.), skin fibroblasts FB were cultured using DMEM medium containing 10% FBS (Invitrogen Corp.), and human vascular endothelial cells HUVEC were cultured using EGM-2 medium (Sanko Junyaku Co., Ltd.). Each of the cells was recovered in Isogen (Nippon Gene Co., Ltd.) and total RNA was extracted in accordance with the protocol provided. Concentration of the purified total RNA was measured with the Nanodrop nucleic acid quantification analyzer (Thermo Scientific Inc.). Each sample was then used to synthesize cDNA in accordance with the manual provided by Invitrogen Corp. using random primers (Invitrogen Corp.) and Superscript II reverse transcriptase (Invitrogen Corp.). Quantitative PCR was then carried out by using the synthesized cDNA as a template and using Light-Cycler FastStart DNA Master PLUS SYBR Green (Roche Diagnostics GmbH) for the reaction reagent and LightCycler (Roche Diagnostics GmbH) for the reaction device. Compositional conditions were in accordance with the Roche protocol. In addition, PCR conditions consisted of initial denaturation for 10 minutes at 95° C. followed by denaturation for 10 seconds at 95° C., annealing for 10 seconds at 60° C. and extension for 10 seconds at 72° C. The sequences of the primers used are indicated below, and expression levels of PDGF gene were measured using software provided with LightCycler.

```
PDGF-A:
Forward primer:
                                     (SEQ ID NO: 1)
    5'-ATACCTCGCCCATGTTCTG-3'

Reverse primer:
                                     (SEQ ID NO: 2)
    5'-GATGCTTCTCTTCCTCCGAA-3'

PDGF-B:
Forward primer:
                                     (SEQ ID NO: 3)
    5'-CTTTAAGAAGGCCACGGTGA-3'

Reverse primer:
                                     (SEQ ID NO: 4)
    5'-CTTCAGTGCCGTCTTGTCAT-3'

PDGF-C:
Forward primer:
                                     (SEQ ID NO: 5)
    5'-TATATTAGGGCGCTGGTGTG-3'

Reverse primer:
                                     (SEQ ID NO: 6)
    5'-ATTAAGCAGGTCCAGTGGCA-3'

PDGF-D:
Forward primer:
                                     (SEQ ID NO: 7)
    5'-TGGGAATCTGTCACAAGCTC-3'

Reverse primer:
                                     (SEQ ID NO: 8)
    5'-CTTTTGACTTCCGGTCATGG-3'
```

-continued

G3PDH:
Forward primer:
(SEQ ID NO: 9)
5'-GCACCGTCAAGGCTGAGAAC-3'

Reverse primer:
(SEQ ID NO: 10)
5'-ATGGTGGTGAAGACGCCAGT-3'

Furthermore, G3PDH was used as an internal standard, and this was used to correct cDNA of the control group during quantification of each gene.

Evaluation of Migration Ability

Commercially available adipose-derived mesenchymal stem cells MSC were purchased and sub-cultured in MesenPro mesenchymal stem cell medium (Invitrogen Corp.). Then, PDGF-AA, PDGF-AB or PDGF-BB (R&D Systems Inc.) was added to StemPro serum-free MSC medium (Invitrogen Corp.) in 24-well culture plates at a concentration of 5 ng/ml to 30 ng/ml, and fibronectin-coated cell inserts (BD Bioscience Inc.) were placed thereon followed by seeding 50,000 MSC suspended in StemPro medium. After culturing overnight in a $CO_2$ incubator, the culture fluid was removed by aspiration. Thereafter, the cell inserts were immersed for 10 minutes in Hoechst 33258-PBS solution, and the nuclei of cells adhered to the cell insert were stained. After washing with PBS, the backs of the cell inserts were observed under a fluorescence microscope and images were captured. Five random images of each cell insert were captured followed by counting the number of cells that transferred to the cell insert.

Localized Sites of PDGF-BB in Human Skin Tissue

Human skin tissue was embedded in OTC Compound frozen tissue embedding medium (Sakura Finetek Japan Co., Ltd.) and 50 μm frozen sections were prepared with a Cryostat frozen section production system (Leica Microsystems GmbH). After air-drying at room temperature, the frozen sections were fixed for 15 minutes at room temperature using chilled acetone cooled for 15 minutes at −20° C. Then, after washing with TBS, blocking treatment was carried out for 30 minutes with serum-free blocking reagent (Dako Corp.), followed by allowing to react overnight at 4° C. with rabbit anti-human PDGF-BB antibody diluted 100-fold with TBST containing 3% BSA (Abcam Inc.) and sheep anti-human CD31 antibody (R&D Systems Inc.). After washing a total of three times consisting of twice for 40 minutes each with TBST and once for 40 minutes with TBS, the frozen sections were allowed to react for 1 hour with secondary antibody labeled with Alexa 488-labeled anti-sheep IgG and Alexa 594-labeled anti-rabbit IgG diluted 200-fold with TBST containing 3% BSA (Invitrogen Corp.). Following reaction, the sections were washed a total of three times consisting of twice for 40 minutes each with TBST and once for 40 minutes with TBS, and after nuclear staining with Hoechst 33258, the sections were observed and imaged using an LSM5 PASCAL confocal fluorescence microscope (Zeiss GmbH).

Vascular Endothelial Cell Tube Formation Assay

After seeding HUVEC labeled with red fluorescent pigment (PKH26 Red Fluorescent, Sigma Corp.) and MSC labeled with green fluorescent pigment (PKH67 Green Fluorescent, Sigma Corp.) in a coated 8-well chamber slide using an in vitro angiogenesis kit, the slide was incubated for 12 hours at 37° C. in the presence of 5% $CO_2$. The status of the tubes that formed was observed using an LSM5 PASCAL confocal fluorescence microscope (Zeiss GmbH) and images were captured. In addition, mouse anti-PDGF receptor neutralizing antibody (R&D Systems Inc.) or mouse IgG coinciding with the isotype were used at a concentration of 5 μg/ml.

Measurement of PDGF Gene Expression Levels in Human Skin by Quantitative PCR

Human skin tissue was frozen with liquid nitrogen, and the tissue was crushed while cooling with liquid nitrogen using a cryopress (Microtech Nichion K.K.). The samples were recovered in Isogen (Nippon Gene Co., Ltd.) and total RNA was extracted from the skin using the protocol provided. The expressed amount of PDGF-B gene was determined in the same manner as previously described using the primers indicated below.

PDGF-B:
Forward primer:
(SEQ ID NO: 11)
5'-CCTGGCATGCAAGTGTGA-3'

Reverse primer:
(SEQ ID NO: 12)
5'-CCAATGGTCACCCGATTT-3'

Staining of Human Mesenchymal Stem Cells in Skin

After fixing human skin tissue for up to 1 week in formalin-phosphate buffer solution, the tissue was embedded in paraffin using an automated embedder (Sakura Finetek Japan Co., Ltd.). Six μm tissue sections were prepared from the resulting human skin paraffin block with a microtome (Leica Microsystems GmbH), and the sections were affixed to an APS coated slide glass followed by flattening and drying on a flattening table (Sakura Finetek Japan Co., Ltd.). The prepared skin tissue slides were de-paraffinized with xylene and subjected to hydrophilic treatment with a mixture of ethanol and water, and after rinsing with TBS buffer, CD34 antigen was activated by subjecting to enzymatic reaction treatment at 37° C. for 15 minutes with 20 μg/ml Proteinase K (Roche Diagnostics GmbH). Then, after thoroughly washing with TBST, blocking treatment was carried out for 15 minutes with a serum-free blocking agent (Dako Corp.), followed by reacting for 1 hour at room temperature with mouse anti-human CD34 antibody (Clone QBEND-10, Abcam Inc.). After washing a total of three times consisting of twice for 15 minutes each with TBST and once for 15 minutes with TBS, the sections were allowed to react for 15 minutes with anti-mouse antibody staining reagent (Histofine Mouse Staining Kit, Nichirei Corp.). Then, after washing a total of three times consisting of twice for 15 minutes each with TBST and once for 15 minutes with TBS, the sections were reacted for 15 minutes with peroxidase-labeled streptavidin (Nichirei Corp.). Following reaction, the sections were washed a total of three times consisting of twice for 15 minutes each with TBST and once for 15 minutes with TBS, followed by carrying out a coloring reaction using Simple Stain DAB solution (Nichirei Corp.). After rinsing with distilled water without counter-staining, dehydration with a mixture of ethanol and water and penetration treatment with xylene were carried out followed by sealing using Mount Quick (Daido Sangyo Co., Ltd.) and a cover glass. Images were captured with the 20× object lens of a differential interference contrast microscope (BX51, Olympus Corp.), and the number of CD34-positive cells in 10 images was counted for each section.

Evaluation of PDGF-B Production Accelerating Action in Vascular Endothelial Cells Human vascular endothelial cells HUVEC were sub-cultured in EGM-2 medium (Sanko Junyaku Co., Ltd.), and the fourth generation cells were suspended in Humedia-EG2 medium not containing VEGF-A (Kurabo Industries Ltd.), followed by disseminating in a collage-coated 24-well multiplate (Asahi Glass Co., Ltd.) at a ratio of 20,000 cells and culturing for 3 to 5 days at 37° C. until the cells reached confluence in the presence of 5% $CO_2$. After replacing the medium with Humedia-EG2 medium (Kurabo Industries Ltd.) containing retinoic acid at 1 μm or 10 μm or DMSO used as a solvent control, culturing was further continued for 2 days. Following completion of culturing, the culture supernatant was recovered and PDGF-BB was quantified in accordance with the protocol provided using Human PDGF-BB Quantikine ELISA Kit (R&D Systems Inc.). In addition, mRNA was extracted and purified from the cultured cells using the RNA extraction reagent, MagNA Pure LC mRNA HS Kit (Roche Diagnostics GmbH), and the automated nucleic acid extraction system, MagNA Pure LC 1.0 Instrument (Roche Diagnostics GmbH) in accordance with the protocol provided. One-step quantitative RT-PCR was then carried out on the PDGF-B gene for each sample using an equal volume of mRNA as template, using the primer pair of SEQ ID NO: 9 and SEQ ID NO: 10, and using QuantiFast SYBR Green RT-PCR Kit (Qiagen Inc.) for the reaction reagent and LightCycler (Roche Diagnostics GmbH) for the reaction apparatus. Compositional conditions were in accordance with the Qiagen protocol. In addition, RT-PCR conditions consisted of carrying out the RT reaction for 20 minutes at 50° C., initial denaturation for 15 minutes at 95° C., denaturation for 15 seconds at 94° C., annealing for 20 seconds at 60° C., and extension for 30 seconds at 72° C. Furthermore, G3PDH was used as an internal standard, and this was used to correct the amount of mRNA of the control group.

Results

Figure 2:
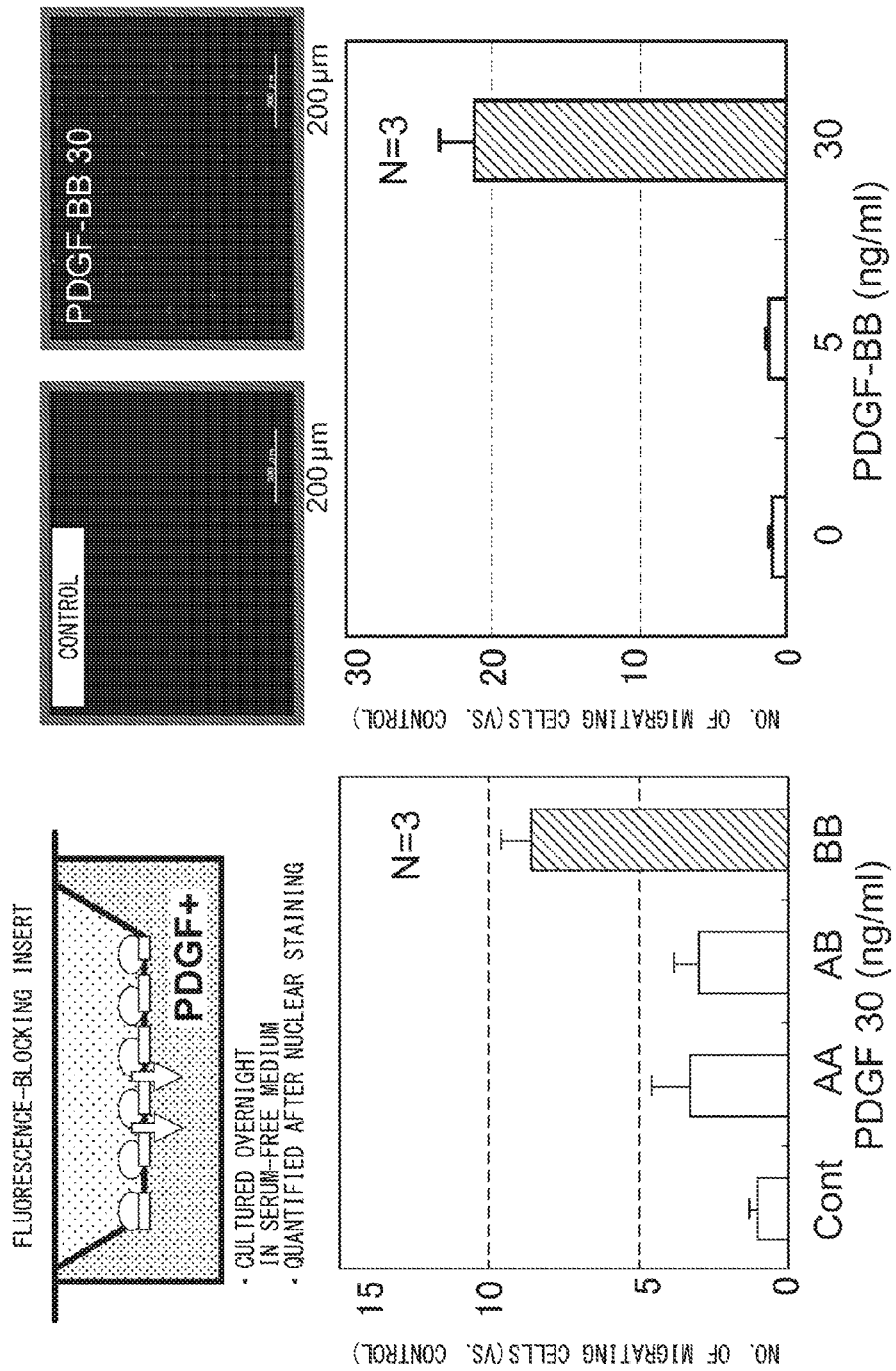
FIG. 2 indicates migration of dermal/adipose-derived stem cells induced by PDGF.

Mesenchymal stem cells have been determined to be locally present at vascular sites in human skin (Japanese Patent Application No. 2009-213291). As a result of comparing expression of the four genes of PDGF-A, PDGF-B, PDGF-C and PDGF-D in skin constituent cells for the purpose of investigating highly expressive molecular species at vascular sites for the PDGF family known as fibroblast migration factors, PDGF-B was determined to be extremely high expressed in HUVEC while hardly expressed at all in FB (FIG. 1). In addition, PDGF-A was determined to be expressed equally in KC, ORSC and HUVEC and at about four times the level of that in FB, while PDGF-C and PDGF-D were expressed at considerably high levels in FB (FIG. 1). Since expression of PDGF-A and PDGF-B was observed in HUVEC, it was decided to investigate the effects of PDGF proteins PDGF-AA, PDGF-AB and PDGF-BB arising from these genes on the migration ability of mesenchymal stem cells. As a result, PDGF-BB was determined significantly enhance the migration ability of stem cells in comparison with PDGF-AA and PDGF-AB (FIG. 2).

Figure 3:
FIG. 3 indicates localization of PDGF-BB in dermis.
Figure 4:
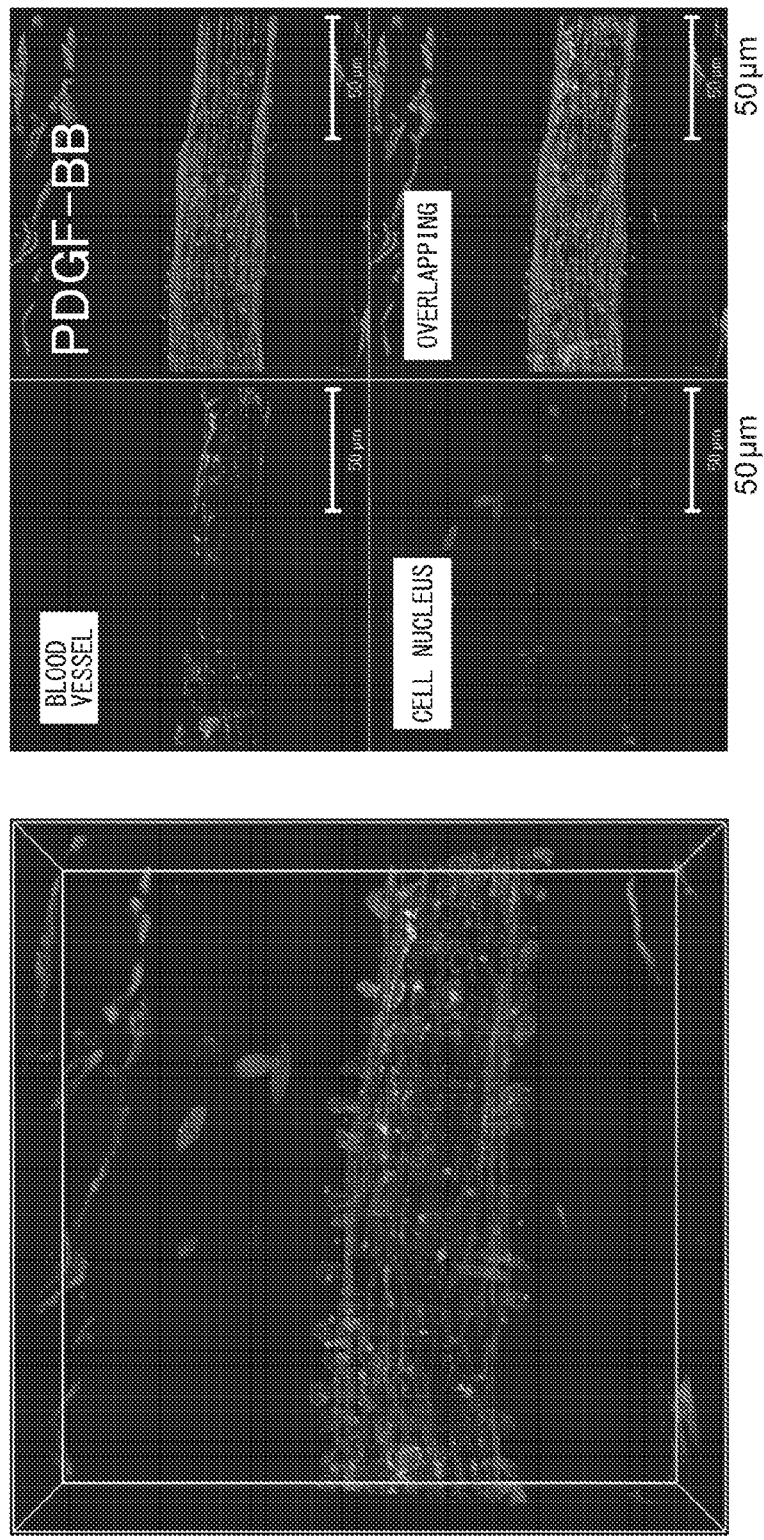
FIG. 4 indicates localization of PDGF-BB in dermis.
Figure 5:
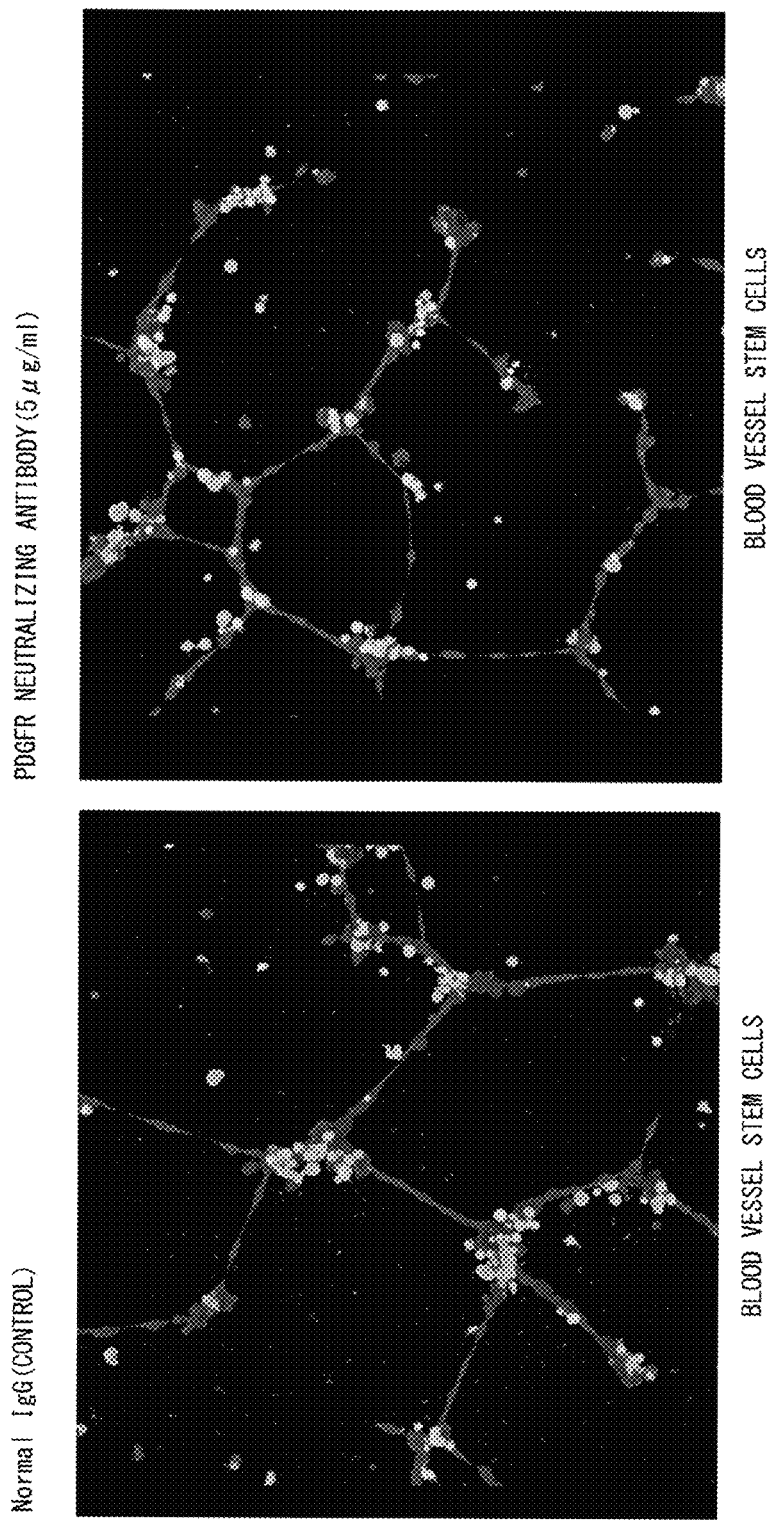
FIG. 5 indicates the effects of PDGF-BB inhibition on accumulation of dermal/adipose-derived stem cells in niches.
Figure 6:
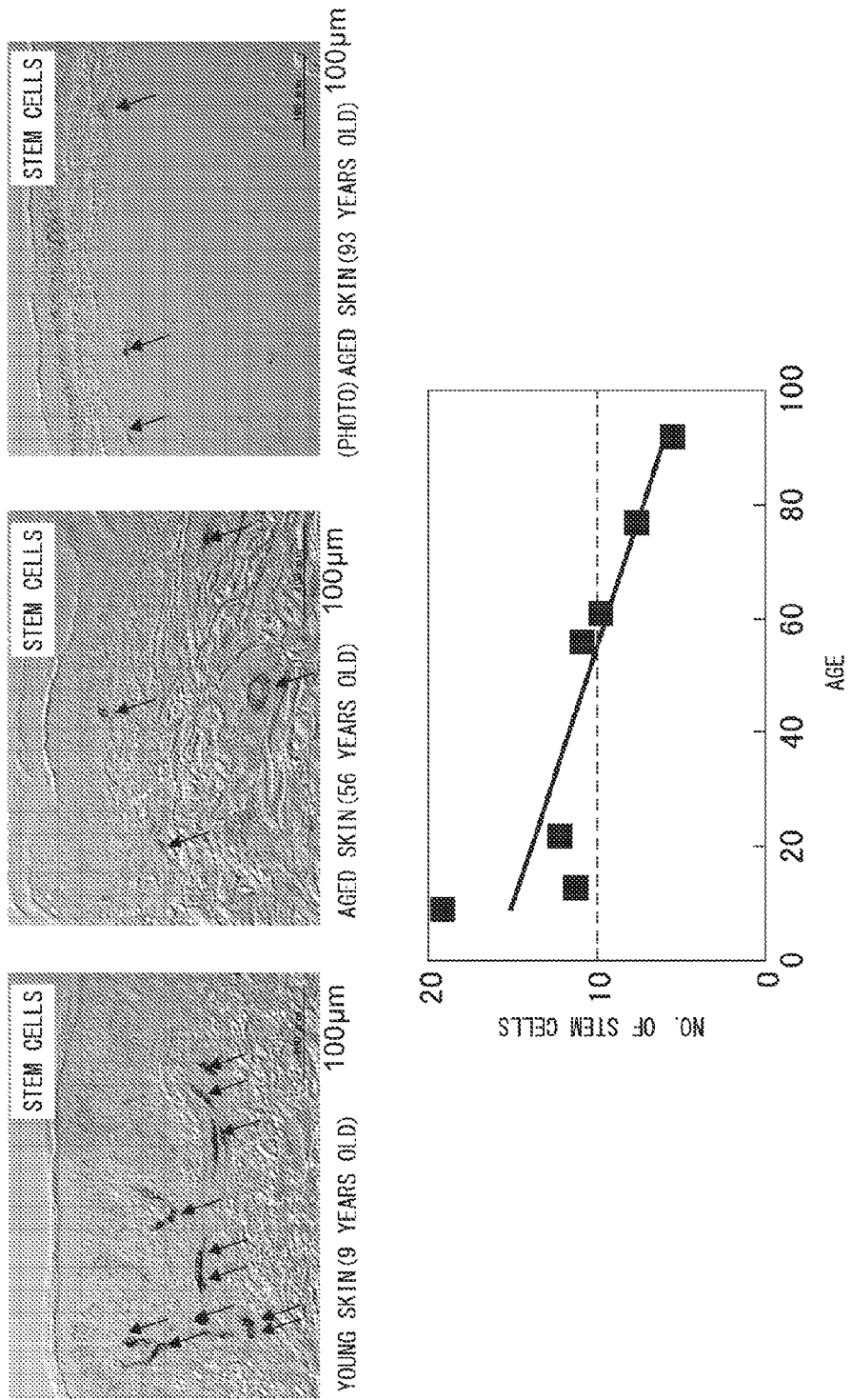
FIG. 6 indicates changes in human dermal/adipose-derived stem cells attributable to aging.
Figure 7:
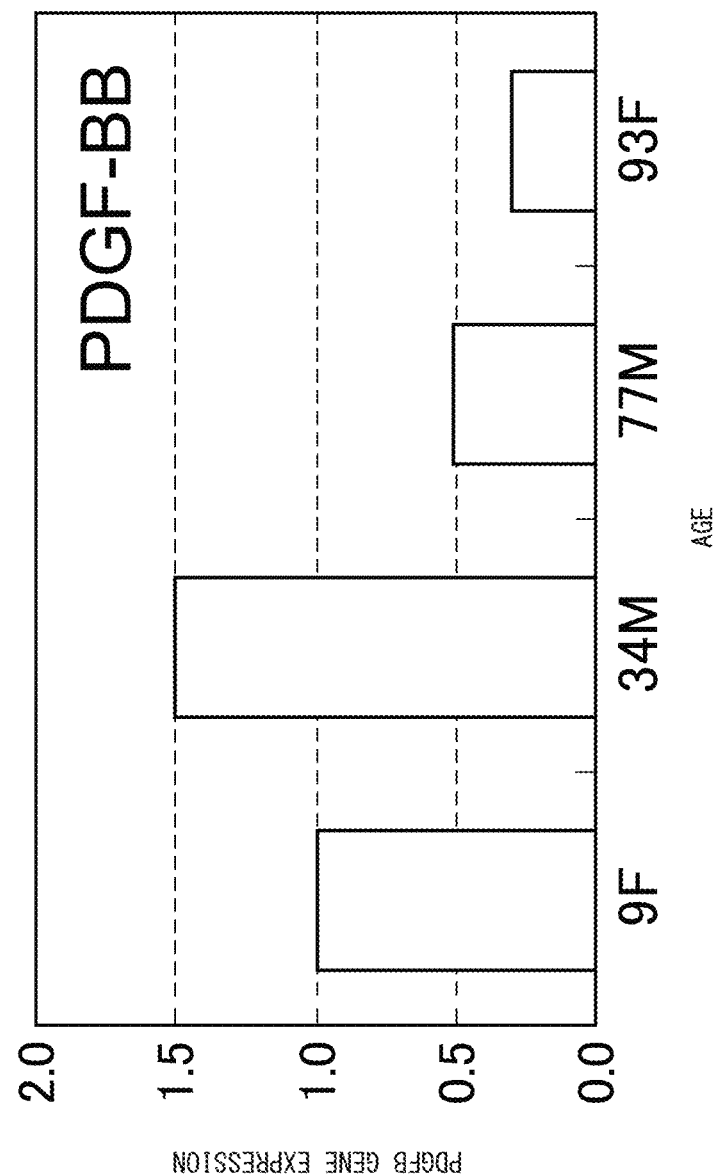
FIG. 7 indicates changes in human dermal/adipose-derived stem cells attributable to aging.

Thereafter, when the localization of PDGF-BB in the dermis and subcutaneous fat was investigated, it was found to be distributed in the same manner as the vascular marker CD31 at sites of large vessels (FIG. 3). When the distribution status at sites of large vessels was observed with a confocal laser microscope, PDGF-BB was found to be present outside vascular endothelial cells and between pericytes (namely, dermal stem cells) (FIG. 4). Moreover, in contrast to nearly all mesenchymal stem cells accumulating at branched portions following their addition in a vascular endothelial cell tube formation assay, accumulation at branched portions was inhibited in the presence of PDGF-BB receptor PDGFRβ neutralizing antibody (FIG. 5), thereby suggesting that PDGF-BB promotes the accumulation of mesenchymal stem cells at vascular sites. When aging changes in mesenchymal stem cells and PDGF-BB were investigated in human skin, it was found that the number of mesenchymal stem cells decreases with age (FIG. 6), and that expression of PDGF-B gene similar decreases as a result of aging (FIG. 7). On the basis of these findings, it is thought that it possible to activate the skin by increasing the number of mesenchymal stem cells by maintaining and accelerating PDGF-BB.

Figure 8:
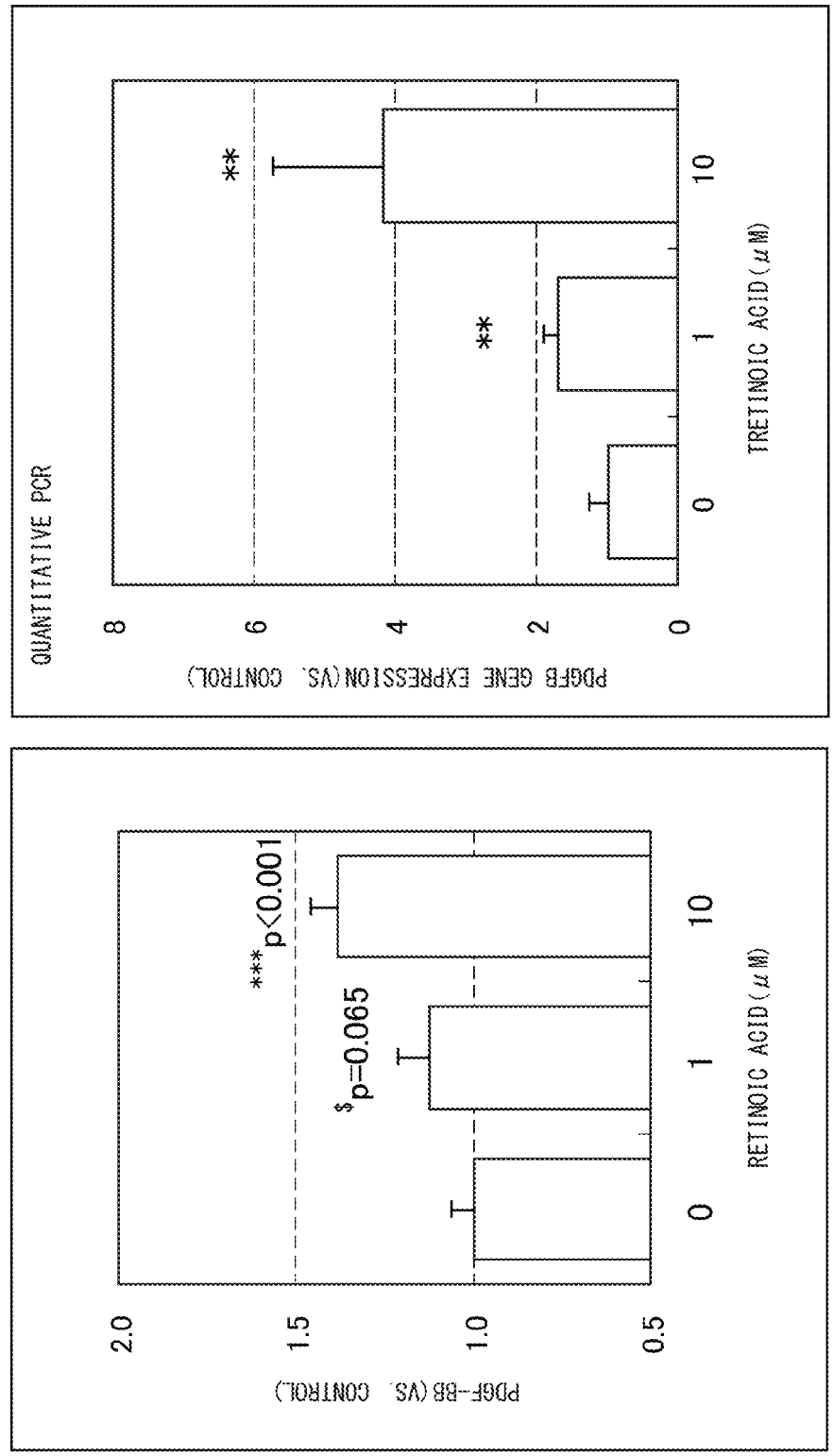
FIG. 8 indicates acceleration of PDGF-BB production by retinoic acid.

Therefore, as a result of investigating drugs that accelerate expression of PDGF-BB by ELISA and quantitative PCR, tretinoin (all-trans retinoic acid) was found to demonstrate concentration-dependent activity (FIG. 8).

The invention claimed is:

1. An in vitro method of screening a candidate drug for use as a skin activator, comprising:

(a) contacting one or more vascular endothelial cells with a candidate drug;

(b) measuring expression of PDGF-BB in the one or more vascular endothelial cells; and (c) comparing, through statistical techniques, the expression of PDGF-BB in the one or more vascular endothelial cells caused by the candidate drug to the expression of PDGF-BB in the one or more vascular endothelial cells caused by a positive control, wherein the positive control is retinoic acid, wherein the candidate drug is a skin activator if it accelerates expression of PDGF-BB, wherein application of the skin activator results in accumulation of mesenchymal stem cells at a vascular site from which one or more vascular endothelial cells originate, and wherein the candidate drug is not a vector designed to introduce a PDGF-BB gene into the one or more vascular endothelial cells.

2. The method according to claim 1 wherein the expression of PDGF-BB in the one or more vascular endothelial cells is measured by reverse transcription polymerase chain reaction for mRNA encoding PDGF-B.

* * * * *

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: PDGF-A Forward Primer

<400> SEQUENCE: 1
atacctcgcc catgttctg                                              19

<210> SEQ ID NO 2
<211> LENGTH: 20
<212> TYPE: DNA
<213> ORGANISM: Artificial Sequence
<220> FEATURE:
<223> OTHER INFORMATION: PDGF-A Reverse Primer

<400> SEQUENCE: 2
gatgcttctc ttcctccgaa                                             20

```
<210> SEQ ID NO 3
<211> LENGTH: 20
<212> TYPE: DNA
<213> ORGANISM: Artificial Sequence
<220> FEATURE:
<223> OTHER INFORMATION: PDGF-B Forward Primer

<400> SEQUENCE: 3
ctttaagaag gccacggtga                                               20

<210> SEQ ID NO 4
<211> LENGTH: 20
<212> TYPE: DNA
<213> ORGANISM: Artificial Sequence
<220> FEATURE:
<223> OTHER INFORMATION: PDGF-B Reverse Primer

<400> SEQUENCE: 4
cttcagtgcc gtcttgtcat                                               20

<210> SEQ ID NO 5
<211> LENGTH: 20
<212> TYPE: DNA
<213> ORGANISM: Artificial Sequence
<220> FEATURE:
<223> OTHER INFORMATION: PDGF-C Forward Primer

<400> SEQUENCE: 5
tatattaggg cgctggtgtg                                               20

<210> SEQ ID NO 6
<211> LENGTH: 20
<212> TYPE: DNA
<213> ORGANISM: Artificial Sequence
<220> FEATURE:
<223> OTHER INFORMATION: PDGF-C Reverse Primer

<400> SEQUENCE: 6
attaagcagg tccagtggca                                               20

<210> SEQ ID NO 7
<211> LENGTH: 20
<212> TYPE: DNA
<213> ORGANISM: Artificial Sequence
<220> FEATURE:
<223> OTHER INFORMATION: PDGF-D Forward Primer

<400> SEQUENCE: 7
tgggaatctg tcacaagctc                                               20

<210> SEQ ID NO 8
<211> LENGTH: 20
<212> TYPE: DNA
<213> ORGANISM: Artificial Sequence
<220> FEATURE:
<223> OTHER INFORMATION: PDGF-D Reverse Primer

<400> SEQUENCE: 8
cttttgactt ccggtcatgg                                               20

<210> SEQ ID NO 9
<211> LENGTH: 20
<212> TYPE: DNA
<213> ORGANISM: Artificial Sequence
<220> FEATURE:
<223> OTHER INFORMATION: G3PDH Forward Primer
```

```
<400> SEQUENCE: 9
gcaccgtcaa ggctgagaac                                              20

<210> SEQ ID NO 10
<211> LENGTH: 20
<212> TYPE: DNA
<213> ORGANISM: Artificial Sequence
<220> FEATURE:
<223> OTHER INFORMATION: G3PDH Reverse Primer

<400> SEQUENCE: 10
atggtggtga agacgccagt                                              20

<210> SEQ ID NO 11
<211> LENGTH: 18
<212> TYPE: DNA
<213> ORGANISM: Artificial Sequence
<220> FEATURE:
<223> OTHER INFORMATION: PDGF-B Forward Primer

<400> SEQUENCE: 11
cctggcatgc aagtgtga                                                18

<210> SEQ ID NO 12
<211> LENGTH: 18
<212> TYPE: DNA
<213> ORGANISM: Artificial Sequence
<220> FEATURE:
<223> OTHER INFORMATION: PDGF-B Reverse Primer

<400> SEQUENCE: 12
ccaatggtca cccgattt                                                18
```